(12) United States Patent
Kenda et al.

(10) Patent No.: US 7,632,856 B2
(45) Date of Patent: Dec. 15, 2009

(54) INDOLONE DERIVATIVES, PROCESSES FOR PREPARING THEM AND THEIR USES

(75) Inventors: Benoît Kenda, Emines (BE); Jean-Phillipe Starck, Gougenheim (FR)

(73) Assignee: UCB Pharma, S.A., Brussels (BE)

(*) Notice: Subject to any disclaimer, the term of this patent is extended or adjusted under 35 U.S.C. 154(b) by 0 days.

(21) Appl. No.: 11/572,383

(22) PCT Filed: Jul. 14, 2005

(86) PCT No.: PCT/EP2005/007668

§ 371 (c)(1),
(2), (4) Date: Jul. 29, 2008

(87) PCT Pub. No.: WO2006/008067

PCT Pub. Date: Jan. 26, 2006

(65) Prior Publication Data

US 2009/0012147 A1    Jan. 8, 2009

(30) Foreign Application Priority Data

Jul. 22, 2004    (EP) .................... 04017296

(51) Int. Cl.
*A61K 31/403*    (2006.01)
*C07D 209/02*    (2006.01)

(52) U.S. Cl. .................. 514/418; 514/408; 514/410; 514/412; 514/415; 548/469; 548/484

(58) Field of Classification Search ............ 514/408, 514/410, 412, 415, 418; 548/469, 484
See application file for complete search history.

(56) References Cited

U.S. PATENT DOCUMENTS 4,624,963 A     11/1986   Kruse et al.
7,129,250 B2 *  10/2006   Jaquith et al. ............ 514/300

FOREIGN PATENT DOCUMENTS

| EP | 0610553 A1 | 8/1994 |
| SU | 841 264 A | 11/1995 |
| WO | 94/29272 A | 12/1994 |
| WO | 01/87887 A | 11/2001 |
| WO | 2004/087658 A | 10/2004 |

OTHER PUBLICATIONS

Patani, George A. Bioisoterism: A rational approach in drug design. Chem. Rev. 96 (1996) 3147-3176.*
Bell et al., "Experimental Antiulcer Drugs. 1. Indole-1-alkanamides and Pyrrole-1-alkanamides", Journal of Medicinal Chemistry, 1977, 537-540, 20(4).
Nilsson et al., Acta Chem. Scand., 1985, 531-548, 39(7).
Bell et al., "Experimental Antiulcer Drugs. 1. Indole-1-alkanamides and Pyrrole-1-alkanamides", Journal of Medicinal Chemistry, 1977, 537-540, 20(4).
Nilsson et al., Beilstein Institute For Organic Chemistry, Frankfurt-Main, DE, Acta Chem. Scand., 1985, 531-548, 39(7), Database Accession No. BRN: 6400176.
Chemical Patents Index, Documentation Abstracts Journal, Section Ch, Nov. 10, 1995, Week 199627, Derwent Publications Ltd., London, GB.

* cited by examiner

*Primary Examiner*—Kamal A Saeed
*Assistant Examiner*—Samantha L Shterengarts
(74) *Attorney, Agent, or Firm*—McDonnell Boehnen Hulbert & Berghoff LLP

(57) ABSTRACT

The present invention relates to indolone derivatives, processes for preparing them, pharmaceutical compositions containing them and their use as pharmaceuticals.

11 Claims, No Drawings

INDOLONE DERIVATIVES, PROCESSES FOR PREPARING THEM AND THEIR USES

CROSS-REFERENCE TO RELATED APPLICATIONS

This is a US National Stage of International Application No. PCT/EP2005/007668, filed Jul. 14, 2005.

BACKGROUND OF THE INVENTION

1. Field of the Invention

The present invention concerns indolone derivatives, processes for preparing them, pharmaceutical compositions containing them and their use as pharmaceuticals.

2. Description of Related Art

Movement and other disorders due to dysfunction of the basal ganglia and related brain structures are of major socio-economic importance. Such disorders can occur as a consequence of inherited or acquired disease, idiopathic neurodegeneration or they may be iatrogenic. The spectrum of disorders is very diverse, ranging from those associated with poverty of movement (akinesia, hypokinesia, bradykinesia, e.g. in parkinsonian symptomatology), hypertonia (e.g. Parkinson's disease, spasticity) to the involuntary movement disorders (hyperkinesias or dyskinesia, e.g. Huntington's disease, dyskinesia induced by L-3,4-dihydroxyphenylalanine (L-DOPA or levodopa), tardive dyskinesia, progressive supernuclear palsy, multiple system atrophy, corticobasal degeneration, Wilson's disease, progressive pallidal atrophy, the dystonias, metabolic neurotransmitter diseases, tics, tremor, Tourette's syndrome, Sydenham's chorea, restless legs syndrome (RLS), chorea and choreathetosis, paroxysmal dyskinesias, myoclonic disorders, Rett syndrome.

Parkinson's disease and related conditions are amongst of the most prevalent diseases associated with poverty of movement. Parkinsonian symptoms are characterized by slowness of movement (bradykinesia), rigidity and/or tremor. Parkinsonian symptoms are seen in a variety of conditions, most commonly in idiopathic parkinsonism (i.e. Parkinson's Disease) but also following treatment of schizophrenia (i.e. neuroleptic-induced parkinsonism), exposure to toxins/drugs and head injury.

It is widely appreciated that the primary pathology underlying Parkinson's disease is degeneration, in the brain, of the dopaminergic projections from the substantia nigra to the striatum. This has led to the widespread use of dopamine-replacing agents (e.g. L-3,4-dihydroxyphenylalanine (L-DOPA) and dopamine agonists) as symptomatic treatments for Parkinson's disease.

L-DOPA therapy currently offers the best symptomatic treatment of Parkinson's disease and a variety of other movement disorders and most patients will require it during the course of their disease. However, patients will develop L-DOPA-associated motor complications. Problems can include motor fluctuations (e.g. delayed "on" response and dose failure, end-of-dose wearing-off, unpredictable "on-off" response, freezing episodes) and the appearance of a range of side-effects which manifest as abnormal involuntary movements, such as dyskinesia (e.g. peak-dose dyskinesia, "off" dystonia, diphasic dyskinesia). Dyskinesias are usually dystonic or choreiform in nature.

The phenomenon of "end-of-dose wearing-off" generally occurs early in the course of the disease. This is the most common and usually the first type of motor fluctuation that develops. As the name implies, the patient develops a loss of response to a dose of medication before taking the next dose. This occurs more often with levodopa than with the dopamine agonists because the agonists have a significantly longer half-life. Over time, fluctuation from mobility to immobility occurs more frequently, becoming more abrupt and disabling. The response to treatment can become unpredictable, many doses of levodopa having a delayed effect or even no effect at all.

Although many attempts have been made to develop agents that will prevent the development and/or the expression of dyskinesias, just a few were made to find a therapeutic tool able to manage motor fluctuations. Until now, only two classes of drug compounds, the catechol-O-methyltransferase (COMT) and monoamine oxydase type B ($MAO_B$) inhibitors, were developed to lengthen the beneficial therapeutic effect of L-DOPA but some of these compounds show adverse effects.

There is therefore, a need for new add-on therapies to L-DOPA which can enhance its efficacy and/or reduce its adverse effects.

European patent application 0 610 553 discloses 6-bromo-2,3-dihydro-3,3-dimethyl-2-oxo-1H-indol-1-acetamide and 6-bromo-2,3-dihydro-3-methyl-2-oxo-1H-indol-1-acetamide as synthesis intermediates.

Russian patent application SU 841264 discloses 2-(2-oxo-2,3-dihydro-1H-indol-1-yl)acetamide and its anticonvulsant activity It has now surprisingly been found that certain indolone derivatives demonstrate therapeutic properties which render them useful in a variety of pharmaceutical indications, and particularly for the symptomatic and/or prophylactic treatment of movement disorders and/or motor fluctuations, in particular in Parkinson's disease.

BRIEF SUMMARY OF THE INVENTION

In one aspect the invention therefore provides a compound having the formula I, a pharmaceutically acceptable salt thereof or stereoisomeric forms thereof,

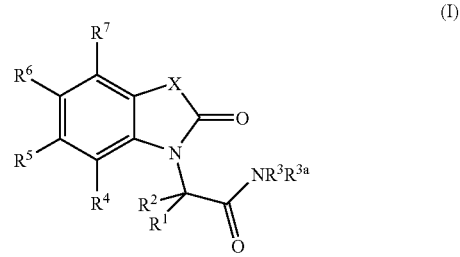

wherein
X is $CH_2$ or $CF_2$;
$R^1$ is selected from hydrogen or C1-4 alkyl optionally substituted by at least one hydroxy;
$R^2$ is selected from hydrogen or C1-4 alkyl optionally substituted by at least one hydroxy;
$R^3$ is selected from hydrogen or unsubstituted C1-4 alkyl;
$R^{3a}$ is selected from hydrogen or unsubstituted C1-4 alkyl;
$R^4$ is selected from hydrogen; halogen; C1-4 alkyl optionally substituted by at least a group selected independently from halogen and a phenyl group; or C1-4 alkoxy optionally substituted by at least a group selected independently from halogen, C1-4 alkoxy and a phenyl group;
$R^5$ is selected from hydrogen; halogen; C1-4 alkyl optionally substituted by at least a group selected independently from halogen and a phenyl group; or C1-4 alkoxy optionally substituted by at least a group selected independently from halogen, C1-4 alkoxy and a phenyl group;

$R^6$ is selected from hydrogen; halogen; C1-4 alkyl optionally substituted by at least a group selected independently from halogen and a phenyl group; or C1-4 alkoxy optionally substituted by at least a group selected independently from halogen, C1-4 alkoxy and a phenyl group;

$R^7$ is selected from hydrogen; halogen; C1-4 alkyl optionally substituted by at least a group selected independently from halogen and a phenyl group; or C1-4 alkoxy optionally substituted by at least a group selected independently from halogen, C1-4 alkoxy and a phenyl group;

with the proviso that if X is $CH_2$, then $R^7$ is different from hydrogen.

In another aspect the invention therefore provides a compound having the formula I, a pharmaceutically acceptable salt thereof or stereoisomeric forms thereof,

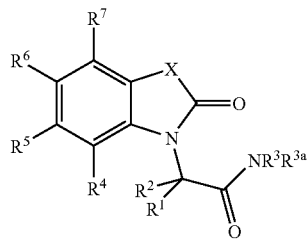

(I)

wherein

X is $CH_2$ or $CF_2$;

$R^1$ is selected from hydrogen or unsubstituted C1-4 alkyl;

$R^2$ is selected from hydrogen or unsubstituted C1-4 alkyl;

$R^3$ is selected from hydrogen or unsubstituted C1-4 alkyl;

$R^{3a}$ is selected from hydrogen or unsubstituted C1-4 alkyl;

$R^4$ is selected from hydrogen; halogen; unsubstituted C1-4 alkyl; or unsubstituted C1-4 alkoxy;

$R^5$ is selected from hydrogen; halogen; unsubstituted C1-4 alkyl; or unsubstituted C1-4 alkoxy;

$R^6$ is selected from hydrogen; halogen; unsubstituted C1-4 alkyl; or unsubstituted C1-4 alkoxy;

$R^7$ is selected from hydrogen; halogen; unsubstituted C1-4 alkyl; trifluoromethyl; or unsubstituted C1-4 alkoxy;

with the proviso that if X is $CH_2$, then $R^7$ is different from hydrogen.

DETAILED DESCRIPTION OF THE INVENTION

The term "halogen", as used herein, represents an atom of chlorine, bromine, fluorine, iodine. Preferred halogens are chlorine, bromine and fluorine.

The term "hydroxy", as used herein, represents a group of the formula —OH.

The term "C1-4 alkyl", as used herein, represents saturated, monovalent hydrocarbon radicals having straight or branched moieties and containing 1-4 carbon atoms. The preferred alkyl groups are methyl and trifluoromethyl.

The term "C1-4 alkoxy", as used herein, represents a group of formula —$OR^a$ wherein $R^a$ is a C1-4 alkyl group, as described above.

The term "phenyl group", as used herein, represents a phenyl optionally substituted by 1 to 3 substituents selected from halogen, C1-4 alkyl, C1-4 alkoxy or cyano.

The term "cyano", as used herein, represents a group of the formula —CN.

In a particular embodiment, the invention provides compounds of formula I wherein X is $CH_2$;

$R^1$ and $R^2$ are selected independently from hydrogen or C1-4 alkyl optionally substituted by at least one hydroxy;

$R^3$ and $R^{3a}$ are selected independently from hydrogen or unsubstituted C1-4 alkyl;

$R^4$, $R^5$ and $R^6$ are selected independently from hydrogen; halogen; C1-4 alkyl optionally substituted by at least a group selected independently from halogen and a phenyl group; or C1-4 alkoxy optionally substituted by at least a group selected independently from halogen, C1-4 alkoxy and a phenyl group;

and $R^7$ is halogen; C1-4 alkyl optionally substituted by at least a group selected independently from halogen and a phenyl group; or C1-4 alkoxy optionally substituted by at least a group selected independently from halogen, C1-4 alkoxy and a phenyl group.

In another particular embodiment, the invention provides compounds of formula I wherein X is $CF_2$;

$R^1$ and $R^2$ are selected independently from hydrogen or C1-4 alkyl optionally substituted by at least one hydroxy;

$R^3$ and $R^{3a}$ are selected independently from hydrogen or unsubstituted C1-4 alkyl;

$R^4$, $R^5$, $R^6$ and $R^7$ are selected independently from hydrogen; halogen; C1-4 alkyl optionally substituted by at least a group selected independently from halogen and a phenyl group; or C1-4 alkoxy optionally substituted by at least a group selected independently from halogen, C1-4 alkoxy and a phenyl group.

Preferably $R^1$ is hydrogen. Preferably $R^2$ is hydrogen. Preferably $R^3$ is hydrogen. Preferably $R^{3a}$ is hydrogen. More preferably $R^1$, $R^2$, $R^3$ and $R^{3a}$ are hydrogen.

Generally $R^4$ is hydrogen or halogen. Usually $R^4$ is hydrogen, chlorine or fluorine. Preferably $R^4$ is hydrogen.

Generally $R^5$ is hydrogen or halogen. Usually $R^5$ is hydrogen or fluorine. Preferably $R^5$ is hydrogen.

Generally $R^6$ is hydrogen; halogen; C1-4 alkyl unsubstituted or substituted by halogen; or C1-4 alkoxy unsubstituted or substituted by C1-4 alkoxy. Preferably $R^6$ is hydrogen, methyl, bromine, chlorine or fluorine. More preferably $R^6$ is hydrogen, chlorine or bromine.

Generally $R^7$ is hydrogen; halogen; C1-4 alkyl unsubstituted or substituted by halogen; or C1-4 alkoxy unsubstituted or substituted by a phenyl group or C1-4 alkoxy. Preferably $R^7$ is hydrogen, chlorine, fluorine or trifluoromethyl. More preferably $R^7$ is hydrogen, chlorine or fluorine. Most preferably, $R^7$ is hydrogen or fluorine.

Combinations of one or more of these preferred compound groups are especially preferred.

Preferred compounds according to the invention are compounds of formula I wherein X is $CH_2$ or $CF_2$; $R^1$, $R^2$, $R^3$, $R^{3a}$, $R^4$ and $R^5$ are hydrogen; and $R^6$ is hydrogen, methyl, bromine, chlorine or fluorine; and $R^7$ is hydrogen, chlorine, fluorine or trifluoromethyl; with the proviso that if X is $CH_2$, then $R^7$ is chlorine or fluorine.

More preferred compounds according to the invention are compounds of formula I wherein X is $CH_2$ or $CF_2$; $R^1$, $R^2$, $R^3$, $R^{3a}$, $R^4$ and $R^5$ are hydrogen; and $R^6$ is hydrogen, chlorine or bromine; and $R^7$ is hydrogen, chlorine or fluorine; with the proviso that if X is $CH_2$, then $R^7$ is chlorine or fluorine.

Most preferred compound according to the invention is compounds of formula I wherein X is $CH_2$; $R^1$, $R^2$, $R^3$, $R^{3a}$, $R^4$ and $R^5$ are hydrogen; $R^6$ is hydrogen; and $R^7$ is fluorine.

In another most preferred embodiment, X is $CF_2$; $R^1$, $R^2$, $R^3$, $R^{3a}$, $R^4$ and $R^5$ are hydrogen; $R^6$ is chlorine or bromine; and $R^7$ is hydrogen.

Preferred individual compounds of the invention are:
2-(4-chloro-2-oxo-2,3-dihydro-1H-indol-1-yl)acetamide;
2-(5-bromo-4-chloro-2-oxo-2,3-dihydro-1H-indol-1-yl)acetamide;
2-(4-fluoro-2-oxo-2,3-dihydro-1H-indol-1-yl)acetamide;
2-(4,5-dichloro-2-oxo-2,3-dihydro-1H-indol-1-yl)acetamide;
2-(3,3-difluoro-2-oxo-2,3-dihydro-1H-indol-1-yl)acetamide;
2-(5-chloro-3,3-difluoro-2-oxo-2,3-dihydro-1H-indol-1-yl)acetamide;
2-(5-bromo-3,3-difluoro-2-oxo-2,3-dihydro-1H-indol-1-yl)acetamide;
2-(3,3-difluoro-5-methyl-2-oxo-2,3-dihydro-1H-indol-1-yl)acetamide;
2-(3,3,5-trifluoro-2-oxo-2,3-dihydro-1H-indol-1-yl)acetamide; and
2-[2-oxo-4-(trifluoromethyl)-2,3-dihydro-1H-indol-1-yl]acetamide.

More preferred compounds of the invention are:
2-(4-chloro-2-oxo-2,3-dihydro-1H-indol-1-yl)acetamide;
2-(4-fluoro-2-oxo-2,3-dihydro-1H-indol-1-yl)acetamide;
2-(5-chloro-3,3-difluoro-2-oxo-2,3-dihydro-1H-indol-1-yl)acetamide; and
2-(5-bromo-3,3-difluoro-2-oxo-2,3-dihydro-1H-indol-1-yl)acetamide.

Most preferred compounds of the invention are:
2-(4-fluoro-2-oxo-2,3-dihydro-1H-indol-1-yl)acetamide;
2-(5-chloro-3,3-difluoro-2-oxo-2,3-dihydro-1H-indol-1-yl)acetamide; and
2-(5-bromo-3,3-difluoro-2-oxo-2,3-dihydro-1H-indol-1-yl)acetamide.

Best results have been obtained with 2-(4-fluoro-2-oxo-2,3-dihydro-1H-indol-1-yl)acetamide.

The "pharmaceutically acceptable salts" according to the invention include therapeutically active, non-toxic base salt forms which the compounds of formula I are able to form.

For example the compounds of formula I containing acidic protons may be converted into their therapeutically active, non-toxic base addition salt forms, e.g. metal or amine salts, by treatment with appropriate organic and inorganic bases. Appropriate base salt forms include, for example but not limited to, ammonium salts, alkali and alkaline earth metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Conversely said salt forms can be converted into the free forms by treatment with an appropriate acid.

Compounds of the formula I and their salts can be in the form of solvates, which are included within the scope of the present invention. Such solvates include for example hydrates, alcoholates and the like.

Some of the compounds of formula I and some of their intermediates have at least one stereogenic center in their structure. This stereogenic center may be present in a R or a S configuration, said R and S notation is used in correspondence with the rules described in Pure Appl. Chem., 45 (1976) 11-30.

The invention also relates to all stereoisomeric forms such as enantiomeric and diastereoisomeric forms of the compounds of formula I or mixtures thereof (including all possible mixtures of stereoisomers).

Some of the compounds of formula I may also exist in tautomeric forms. Such forms although not explicity indicated in the above formula are intended to be included within the scope of the present invention.

With respect to the present invention reference to a compound or compounds is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of formula I according to the invention can be prepared analogously to conventional methods as understood by the person skilled in the art of synthetic organic chemistry.

According to one embodiment, some compounds having the general formula I wherein X is $CF_2$, may be prepared by alkylation of a compound of formula II with a compound of formula III according to the equation:

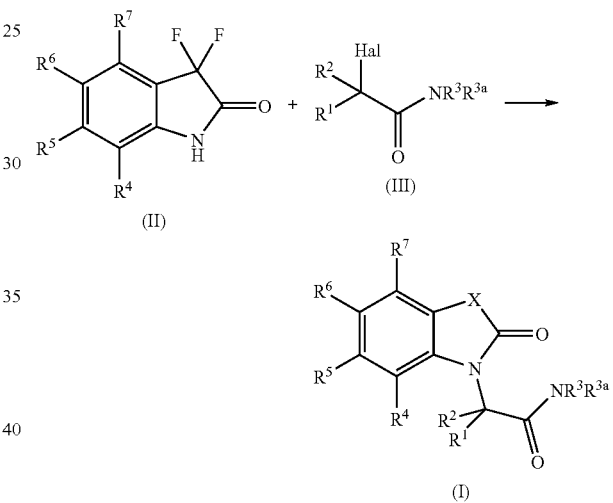

wherein Hal is a halogen atom, preferably bromine or chlorine, and X, $R^1$, $R^2$, $R^3$, $R^{3a}$, $R^4$, $R^5$, $R^6$ and $R^7$ have the same definitions as described above.

This reaction may be carried out with a strong base, for example sodium hydride, at a temperature comprised between 0 and 40° C. and in an inert solvent, for example DMF under an inert atmosphere, or as described in patent GB 1,309,692 (UCB).

Compounds of formula II may be prepared by reaction of a compound of formula IV with diethylaminosulphur trifluoride (DAST) according to the equation:

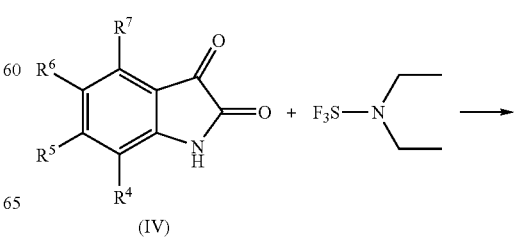

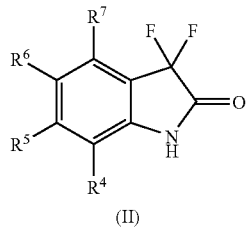

(II)

wherein $R^4$, $R^5$, $R^6$ and $R^7$ have the same definitions as described above.

This reaction may be carried out in an inert solvent, at a temperature comprised between 0 and 100° C.

Compounds of formula IV are commercially available or may be prepared according to methods described in: Smith K., El-Hiti G. A., Hawes A. C., Synlett (1999), 945-947; Lackey K., Sternbach D. D., Synthesis (1993), 10, 993; or Organic Synthesis, Collective Volume I, Second Edition, Gilman H. & Blatt A. H., J. Wiley & Sons Inc., 327-330.

According to another embodiment, some compounds having the general formula I, wherein X is $CH_2$, may be prepared by oxidative bromination of the corresponding indole of formula (V) followed by the reduction of compound (VI) according to the equation:

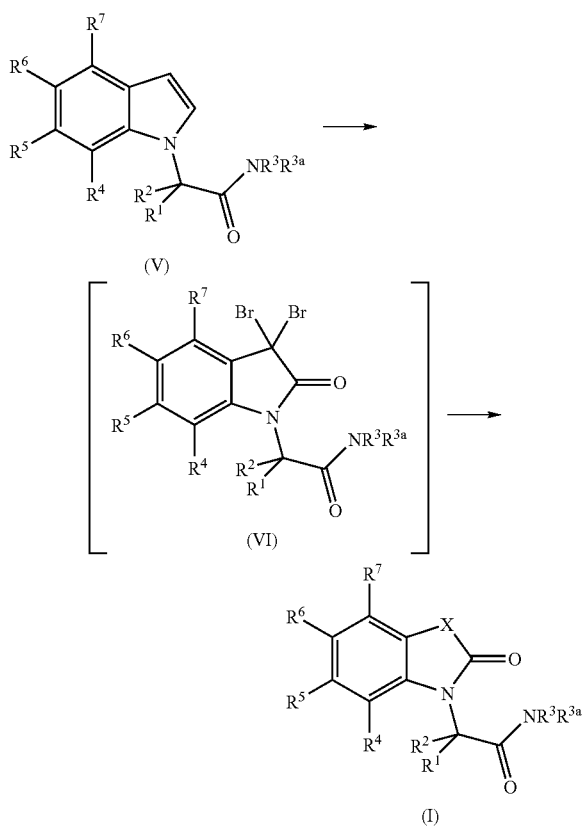

wherein $X, R^1, R^2, R^3, R^{3a}, R^4, R^5, R^6$ and $R^7$ have the same definitions as described above.

This reaction may be carried out as described in: Marfat A., Carta M. P., Tetrahedron Lett. (1987), 28, 4027-4031.

Compounds of formula V may be prepared by alkylation of a compound of formula VII with a compound of formula III according to the equation:

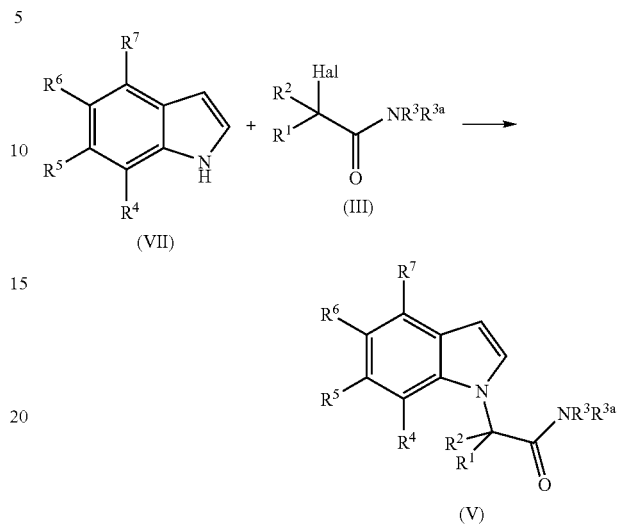

wherein Hal is an halogen atom, preferably bromine or chlorine.

This reaction may be carried out in the presence of a strong base, preferably sodium hydride, at a temperature comprised between 0 and 40° C., in an inert solvent, for example DMF, under an inert atmosphere, or as described in patent GB 1,309,692 (UCB).

According to another embodiment, some compounds having the general formula I may be prepared by halogenation of the corresponding compound of formula I wherein $R^6$ is a hydrogen with a N-halosuccinimide according to the procedure described in: Castanet A.-S., Colobert F., Broutin P.-E., Tetrahedron Lett. (2002), 43, 5047-5048.

In one embodiment, the present invention concerns a compound of formula V or stereoisomeric forms thereof,

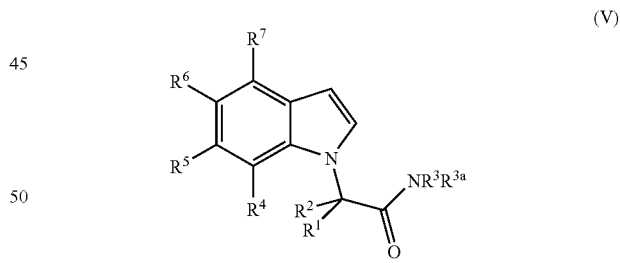

wherein $R^1$ and $R^2$ are selected independently from hydrogen or C1-4 alkyl optionally substituted by at least one hydroxy;

$R^3$ and $R^{3a}$ are selected independently from hydrogen or unsubstituted C1-4 alkyl;

$R^4$, $R^5$ and $R^6$ are selected independently from hydrogen; halogen; C1-4 alkyl optionally substituted by at least a group selected independently from halogen and a phenyl group; or C1-4 alkoxy optionally substituted by at least a group selected independently from halogen, C1-4 alkoxy and a phenyl group; and $R^7$ is halogen; C1-4 alkyl optionally substituted by at least a group selected independently from halogen and a phenyl group; or C1-4 alkoxy optionally substituted by at least a group selected independently from halogen, C1-4 alkoxy and a phenyl group.

Preferably, the compounds of formula V are selected from the group consisting of 2-(4-fluoro-1H-indol-1-yl)acetamide; 2-(4-chloro-1H-indol-1-yl)acetamide and 2-[4-(trifluoromethyl)-1H-indol-1-yl]acetamide.

The present invention also concerns the synthesis intermediate 3,3,5-trifluoro-1,3-dihydro-2H-indol-2-one.

The above compounds are particularly useful as synthesis intermediates.

It has now been found that compounds of formula I, their pharmaceutically acceptable salts, or stereoisomeric forms thereof are useful in a variety of pharmaceutical indications.

For example, the compounds of formula I according to the invention are useful for the symptomatic and/or prophylactic treatment of movement disorders and/or motor fluctuations, in particular in Parkinson's disease.

In another aspect the invention therefore provides the therapeutical use of compounds of formula I, pharmaceutically acceptable salts thereof or stereoisomeric forms thereof.

In another aspect the invention provides the use of compounds of formula I, or pharmaceutically acceptable salts thereof, for the symptomatic and/or prophylactic treatment of motor fluctuations and/or dyskinesia in Parkinson's patients before or during exposure to dopamine replacement therapy.

The compounds of formula I according to the invention may also be used for the treatment and the prevention of idiopathic Parkinson's disease and other Parkinsonian syndromes.

Additionally, the compounds of formula I according to the invention may be used for the treatment and the prevention of movement disorders.

The compounds of formula I according to the invention may be administered in conjunction with an anti-parkinsonian or any other existing therapy. For example, compounds of formula I may be useful as adjunct therapy in Parkinson's disease to reduce the side-effects experienced with those treatments on long term use, including but not limited to L-DOPA (motor fluctuations and dyskinesia). The compounds may also be used wherein the anti-parkinsonian therapy is one of cell implantation/transplantation, gene therapy, subthalamic nucleus lesions/deep brain stimulation and GPi lesion/deep brain stimulation.

The compounds of formula I may be used to protect against neurodegeneration and may be used in conjunction with neuroprotective agents.

The compounds of formula I may be used to treat neuroleptic-induced Parkinsonism and tardive dyskinesia and could be administered in conjunction with antipsychotic agents.

The compounds of formula I according to the invention may also be used for the treatment of schizophrenia, or other psychotic disorders.

The compounds of the invention may also be used in the treatment of mood disorders.

The compounds of formula I according to the invention may also be used in the treatment of anxiety disorders.

The compounds of formula I according to the invention may also be useful in the treatment of substance-related disorders.

The compounds of formula I according to the invention may also be used in the treatment of delirium, dementia, amnestic and other cognitive disorders (memory, frontal and attentional problems).

The compounds of formula I according to the invention can also be used in the treatment of sexual disorders, sleep disorders, eating disorders (anorexia/bulimia nervosa), personality disorders, factitious disorders, dissociative disorders, emesis, aggression, autism, vertigo, circadian rhythm disorders, convulsion, seizure, epilepsy, gastric motility disorders, attention deficit disorder, reward deficiency syndrome, attention deficit hyperactivity disorder (ADHD), migraine, trigeminal and other neuralgias, chronic pain, neuropathic pain, cerebral ischemia, cardiac arrhythmia, myotonia, stroke, neonatal cerebral haemorrhage, amyotrophic lateral sclerosis, spasticity and degenerative diseases, bronchial asthma, asthmatic status and allergic bronchitis, asthmatic syndrome, bronchial hyperreactivity and bronchospastic syndromes as well as allergic and vasomotor rhinitis and rhinoconjunctivitis.

Thus, the present invention also concerns a compound having the formula I or a pharmaceutically acceptable salt thereof or stereoisomeric forms thereof as defined above for use as a medicament.

In a further aspect, the present invention concerns also the use of a compound of formula I or a pharmaceutically acceptable salt thereof for the manufacture of a medicament for the treatment of neurological, psychiatric and other disorders such as mentioned above.

In particular, the present invention concerns the use of a compound of formula I or a pharmaceutically acceptable salt thereof for the manufacture of a medicament for the treatment of motor fluctuations and/or dyskinesia in Parkinson's patients before or during exposure to dopamine replacement therapy, idiopathic Parkinson's disease and other Parkinsonian syndromes, movement disorders, psychotic disorders, mood disorders, anxiety disorders, substance-related disorders, delirium and dementia.

The methods of the invention comprise administration to a mammal (preferably human) suffering from above mentioned conditions or disorders, of a compound of formula I according to the invention in an amount sufficient to alleviate or prevent the disorder or condition.

The compound is conveniently administered in any suitable unit dosage form, including but not limited to one containing 3 to 7000 mg, preferably 5 to 500 mg of active ingredient per unit dosage form.

The term "treatment" as used herein includes symptomatic treatment, curative treatment and prophylactic treatment.

By "symptomatic" is meant the efficaciousness of the active compound in treating the current episode.

By "curative" is meant efficacy in treating the appearance of symptomatic episodes of a disorder or condition.

By "prophylactic" is meant prevention of the occurrence or recurrence of a disorder or condition. In particular we mean the prevention of any induction of the recurrent episodes and the possibility to depress the manifestation of motor fluctuation and dyskinesia.

By "motor fluctuations" is meant the development in a L-DOPA-treated subject of these four different phenomena: delayed "on" response and dose failures, end-of-dose wearing-off, unpredictable "on-off" response and freezing episodes.

By "end-of-dose wearing-off" is meant the loss of response to a dose of medication before taking the next dose.

The term "dyskinesia" is defined as the development in a subject of abnormal involuntary movements. This appears in patients with Huntington's disease, in Parkinson's disease patients exposed to chronic dopamine replacement therapy, and in Schizophrenia patients exposed to chronic treatment with neuroleptics. Dyskinesias, as a whole, are characterised by the development in a subject of abnormal involuntary movements. One way in which dyskinesias may arise is as a side-effect of dopamine replacement therapy for parkinsonism or other basal ganglia-related movement disorders.

The terms "idiopathic Parkinson's disease and other Parkinsonian syndromes", include, but are not limited to, genetic Parkinsonisms, multiple system atrophy, progressive supranuclear palsy, corticobasal degeneration, Fahr's disease, post-encephalitic parkinsonism, parkinsonism resulting from head injury, drug induced parkinsonisms (e.g. following treatment of schizophrenia and other psychiatric disorders), drug intoxication (e.g. with MPTP-contaminated heroin), toxin-induced Parkinsonism (e.g. following carbon monoxide or manganese poisoning), treatment of Wilson's disease, vascular Parkinsonism, and other Parkinsonian syndromes.

The term "Parkinsonian syndrome" relates to a syndrome characterized by slowness of movement (bradykinesia), rigidity and/or tremor. Parkinsonian syndromes are seen in a variety of conditions, most commonly in idiopathic Parkinsonism (i.e. Parkinson's Disease) but also following treatment of schizophrenia, exposure to toxins/drugs and head injury. It is widely appreciated that the primary pathology underlying Parkinson's disease is degeneration, in the brain, of the dopaminergic projection from the substantia nigra to the striatum. This has led to the widespread use of dopamine-replacing agents (e.g. L-DOPA and dopamine agonists) as symptomatic treatments for Parkinson's disease and such treatments have been successful in increasing the quality of life of patients suffering from Parkinson's disease. However, dopamine-replacement treatments do have limitations, especially following long-term treatment. Problems can include a wearing-off of the anti-parkinsonian efficacy of the treatment and the appearance of a range of side-effects which manifest as abnormal involuntary movements, such as dyskinesias.

By "movement disorder" is meant neurological motor disorders manifested by slowness or poverty of movement (bradykinesia or hypokinesia, such as that seen in parkinsonian disorders) at one end of the spectrum and abnormal involuntary movement (hyperkinesias) such as tremor, dystonia, athetosis, chorea, ballism, tics, myoclonus, restless legs syndrome, stereotypies, akathisias, and other dyskinesias at the other. Movement disorders include, but are not limited to tremors (e.g. physiological, essential, dystonic, primary writing, orthostatic, neuropathic, cerebellar tremor, etc.), choreas (e.g. in Huntingston's disease, Haw River syndrome, neuroacanthocytosis, McLeod syndrome, benign hereditary chorea, Sydenham's chorea, ballismus, senile chorea, etc.), tardive dyskinesia, the dystonias (e.g. childhood onset generalized primary dystonia, adult-onset primary focal and segmental dystonia, X-linked dystonia-Parkinsonism, dopa-responsive dystonia, rapid-onset dystonia, post-traumatic dystonia, tardive dystonia, paroxysmal kinesigenic dyskinesia, paroxysmal nonkinesigenic dyskinesia, secondary paroxysmal dyskinesia, and other paroxysmal dyskinesias, etc.), tics including Tourette's syndrome and adult-onset tic disorders, post-infectious autoimmune neuropsychiatric disorders associated with streptococcal exposure (PANDAS), myoclonic disorders (e.g. essential, posthypoxic, startle, spinal, propriospinal, toxin- and drug-induced myoclonus etc.), and other movement disorders such as hemifacial spasm, stiff person syndrome, painful legs-moving toes syndrome and restless legs syndrome.

The term "psychotic disorders" includes but is not limited to schizophrenia, schizophreniform disorder, schizoaffective disorder, delusional disorder, brief psychotic disorder, shared psychotic disorder, psychotic disorder due to a general medical condition, substance-induced psychotic disorder, postpartum psychiatric syndromes, and psychotic disorder not otherwise specified.

The term "mood disorders" includes but is not limited to depression, major depressive disorder, dysthimic disorder, depression disorder not otherwise specified, mania, bipolar I disorder, bipolar II disorder, cyclothymic disorder, bipolar disorder not otherwise specified, mood disorder due to a general medical condition, substance-induced mood disorder, mood disorder not otherwise specified, The term "anxiety disorders" includes but is not limited to panic attack, agoraphobia, panic disorder with/without agoraphobia, agoraphobia without history of panic disorder, specific phobia, social phobia, obsessive-compulsive disorder, posttraumatic stress disorder, acute stress disorder, generalized anxiety disorder, anxiety disorder due to a general medical condition, substance-induced anxiety disorder, anxiety disorder not otherwise specified. Generally the term "anxiety" as used herein refers to a feeling of apprehension or fear. Anxiety is often accompanied by physical symptoms, including twitching or trembling, muscle tension, headaches, sweating, dry mouth, difficulty swallowing and/or abdominal pain.

The term "substance-related disorders" includes more specifically substance use disorders (substance dependence, substance abuse), substance-induced disorders (substance intoxication, substance withdrawal, substance-induced mental disorders), alcohol-related disorders, amphetamine-related disorders, caffeine-related disorders, cannabis-related disorders, cocaine-related disorders, hallucinogen-related disorders, inhalant-related disorders, nicotine-related disorders, opioid related disorders, phencyclidine-related disorders, sedative-hypnotic or anxiolytic-related disorders, other (unknown) substance-related disorders.

The term "delirium" refers to a disturbance of consciousness and a change in cognition that develop over a short period of time (delirium due to a general medical condition, substance-induced delirium, delirium due to multiple etiologies, delirium not otherwise specified).

The term "amnestic disorders" as used herein refers to a disturbance in memory that is either due to the direct physiological effects of a general medical condition or due to the persisting effects of a substance.

The term "bipolar disorders" as used herein refers to those disorders classified as Mood Disorders according to the Diagnostic and Statistical Manual of Mental Disorders, 4th edition (Diagnostic and Statistical Manual of Mental Disorders (DSM-IV TM), American Psychiatry Association, Washington, D.C., 1994). Bipolar disorders are generally characterised by spontaneously triggered repeated (i.e. at least two) episodes in which the patient's hyperexcitability, activity and mood are significantly disturbed, this disturbance consisting on some occasions of an elevation of mood and increased energy and activity (mania or hypomania), and in other occasions a lowering of mood and decreased energy and activity (depression). Bipolar disorders are separated into four main categories in the DSM-UV (bipolar I disorder, bipolar II disorder, cyclothymia, and bipolar disorders not otherwise specified).

The term "manic episode", as used herein refers to a distinct period during which there is an abnormally and persistently elevated, expansive, or irritable mood with signs of pressured speech and psychomotor agitation.

The term "hypomania", as used herein refers to a less extreme manic episode, with lower grade of severity.

The term "major depressive episode", as used herein refers to a period of at least 2 weeks during which there is either depressed mood or the loss of interest or pleasure in nearly all activities with signs of impaired concentration and psychomotor retardation.

The term "mixed episode", as used herein refers to a period of time (lasting at least 1 week) in which the criteria are met both for a manic episode and for a major depressive episode nearly every day.

The term "chronic pain" as used herein refers to the condition gradually being recognised as a disease process distinct from acute pain. Conventionally defined as pain that persists beyond the normal time of healing, pain can also be considered chronic at the point when the individual realises that the pain is going to be a persistent part of their lives for the foreseeable future. It is likely that a majority of chronic pain syndromes involves a neuropathic component, which is usually harder to treat than acute somatic pain.

The term "neuropathic pain" as used herein refers to pain due to a dysfunctional nervous system, sometimes occurring following injury to the central nervous system (central pain), but more often caused by damage to peripheral nerves (painful peripheral neuropathy). Neuropathic pain is most likely caused by neural hyperexcitation in partially damaged nerves. Several types of painful peripheral neuropathy, which may share some underlying pathogenic mechanisms, have been distinguished, such as: (1) postraumatic painful peripheral neuropathy; (2) phantom limb pain; (3) facial (trigeminal) pains; (4) postherpetic neuralgia; (5) painful diabetic neuropathy; (6) neuropathies due to cancer tumors; (7) neuropathies induced by treatment with anti-neoplastic agents; and (8) nerve damage associated with demyelinating disease, such as multiple sclerosis. In neuropathic pain, painful reactions appear in response to normally neutral stimuli (allodynia) or as exaggerated reactions to painful stimuli (hyperalgesia). Spontaneous pain, not provoked by external stimuli, also occurs in neuropathic pain, and is the most difficult form of pain to measure and treat.

The term "tics" refers to common and often disabling neurological disorders. They are frequently associated with behaviour difficulties, including obsessive-compulsive disorder, attention deficit hyperactivity disorder and impulse control. Tics are involuntary, sudden, rapid, repetitive, nonrhythmic stereotypic movements or vocalizations. Tics are manifested in a variety of forms, with different durations and degrees of complexity. Simple motor tics are brief rapid movements that often involve only one muscle group. Complex motor tics are abrupt movements that involve either a cluster of simple movements or a more coordinated sequence of movements. Simple vocal tics include sounds such as grunting, barking, yelping, and throat clearing. Complex vocal tics include syllables, phrases, repeating other people's words and repeating one's own words.

The term "tremor" refers to an involuntary, rhythmical, oscillatory movement of a body part. Tremor can be phenomenologically defined as tremor at rest or associated with an action. Such an action can be postural (maintenance of a limb position), kinetic (movement-related), or intentional (at the end of a purposeful movement). Etiologically, tremor most often occurs in Parkinson's disease (Parkinsonian rest tremor) and in essential tremor (postural and kinetic tremor), which consists of hereditary and age-related forms. Tremor may also occur in dystonia and in multiple sclerosis. Other tremors, which can arise from various etiologies, are cerebellar (intentional tremor) and Holmes' midbrain tremor (postural tremor). Tremor can also be an exaggerated form of normal physiological tremor. Apart from the behavioural context in which tremor occurs, tremor frequency is an important criterion to distinguish between various forms of tremor. Essential tremor has the highest incidence of all tremors. As it is age-related, it can be expected to increase in aging populations. Animal models and clinical data indicate that essential tremor may be primarily based on a brainstem (inferior olivary nucleus)—cerebellar dysfunction, whereas Parkinsonian tremor probably originates from abnormal activity within the basal ganglia. Excessive synchronization and/or hyperexcitation in neuronal circuits may underlie tremor activity.

The invention concerns also use of a compound of formula I for the manufacture of a medicament for the treatment of the symptomatic and/or prophylactic treatment of movement disorders and/or motor fluctuations, in particular in Parkinson's disease.

The expression "cognitive disorders" as used herein refers to disturbances of cognition, which encompasses perception, learning and reasoning or in other terms the physiological (mental/neuronal) process of selectively acquiring, storing, and recalling information.

The expression "attention-deficit hyperactivity disorder" (ADHD) as used herein refers to a problem with inattentiveness, over-activity, impulsivity, or a combination of these. For these problems to be diagnosed as ADHD, they must be out of the normal range for the child's age and development. The term "attention-deficit disorder" (ADD) is also commonly used for the same disorder.

The expression "Alzheimer's disease" (AD) as used herein refers to a progressive, neurodegenerative disease characterized in the brain by abnormal clumps (amyloid plaques) and tangled bundles of fibers (neurofibrillary tangles) composed of misplaced proteins. Age is the most important risk factor for AD; the number of people with the disease doubles every 5 years beyond age 65. Three genes have been discovered that cause early onset (familial) AD. Other genetic mutations that cause excessive accumulation of amyloid protein are associated with age-related (sporadic) AD. Symptoms of AD include memory loss, language deterioration, impaired ability to mentally manipulate visual information, poor judgment, confusion, restlessness, and mood swings. Eventually AD destroys cognition, personality, and the ability to function. The early symptoms of AD, which include forgetfulness and loss of concentration, are often missed because they resemble natural signs of aging.

The expression "Parkinson's disease" (PD) as used herein refers to a group of conditions called motor system disorders, which are the result of the loss of dopamine-producing brain cells. The four primary symptoms of PD are tremor, or trembling in hands, arms, legs, jaw, and face; rigidity, or stiffness of the limbs and trunk; bradykinesia, or slowness of movement; and postural instability, or impaired balance and coordination. As these symptoms become more pronounced, patients may have difficulty walking, talking, or completing other simple tasks. PD usually affects people over the age of 50. Early symptoms of PD are subtle and occur gradually. In some people the disease progresses more quickly than in others. As the disease progresses, the shaking, or tremor, which affects the majority of PD patients may begin to interfere with daily activities. Other symptoms may include depression and other emotional changes; difficulty in swallowing, chewing, and speaking; urinary problems or constipation; skin problems; and sleep disruptions.

The term "mild-cognitive impairment" as used herein refers to a transitional stage of cognitive impairment between normal aging and early Alzheimer's disease. It refers particularly to a clinical state of individuals who are memory impaired but are otherwise functioning well and do not meet clinical criteria for dementia.

The term "dementia" as used herein refers to a group of symptoms involving progressive impairment of brain function. American Geriatrics Society refers to dementia as a condition of declining mental abilities, especially memory. The person will have problems doing things he or she used to be able to do, like keep the check book, drive a car safely, or plan a meal. He or she will often have problems finding the right words and may become confused when given too many things to do at once. The person with dementia may also change in personality, becoming aggressive, paranoid, or depressed.

The term "schizophrenia" as used herein refers to a group of psychotic disorders characterized by disturbances in thought, perception, attention, affect, behavior, and communication that last longer than 6 months. It is a disease that makes it difficult for a person to tell the difference between real and unreal experiences, to think logically, to have normal emotional responses to others, and to behave normally in social situations.

The term "anxiety" as used herein refers to a feeling of apprehension or fear. Anxiety is often accompanied by physical symptoms, including twitching or trembling, muscle tension, headaches, sweating, dry mouth, difficulty swallowing and/or abdominal pain.

The term "depression" as used herein refers to a disturbance of mood and is characterized by a loss of interest or pleasure in normal everyday activities. People who are depressed may feel "down in the dumps" for weeks, months, or even years at a time. Some of the following symptoms may be symptoms of depression: persistent sad, anxious, or "empty" mood; feelings of hopelessness, pessimism; feelings of guilt, worthlessness, helplessness; loss of interest or pleasure in hobbies and activities that were once enjoyed, including sex; decreased energy, fatigue, being "slowed down"; difficulty concentrating, remembering, making decisions; insomnia, early-morning awakening, or oversleeping; appetite and/or weight loss or overeating and weight gain; thoughts of death or suicide; suicide attempts; restlessness, irritability; persistent physical symptoms that do not respond to treatment, such as headaches, digestive disorders, and chronic pain.

The term "epilepsy" as used herein refers a brain disorder in which clusters of nerve cells, or neurons, in the brain sometimes signal abnormally. In epilepsy, the normal pattern of neuronal activity becomes disturbed, causing strange sensations, emotions, and behavior or sometimes convulsions, muscle spasms, and loss of consciousness. Epilepsy is a disorder with many possible causes. Anything that disturbs the normal pattern of neuron activity—from illness to brain damage to abnormal brain development—can lead to seizures. Epilepsy may develop because of an abnormality in brain wiring, an imbalance of nerve signaling chemicals called neurotransmitters, or some combination of these factors. Having a seizure does not necessarily mean that a person has epilepsy. Only when a person has had two or more seizures is he or she considered to have epilepsy.

The term "seizure" as used herein refers to a transient alteration of behaviour due to the disordered, synchronous, and rhythmic firing of populations of brain neurones.

The term "migraine" as used herein means a disorder characterised by recurrent attacks of headache that vary widely in intensity, frequency, and duration. The pain of a migraine headache is often described as an intense pulsing or throbbing pain in one area of the head. It is often accompanied by extreme sensitivity to light and sound, nausea, and vomiting. Some individuals can predict the onset of a migraine because it is preceded by an "aura," visual disturbances that appear as flashing lights, zig-zag lines or a temporary loss of vision. People with migraine tend to have recurring attacks triggered by a lack of food or sleep, exposure to light, or hormonal irregularities (only in women). Anxiety, stress, or relaxation after stress can also be triggers. For many years, scientists believed that migraines were linked to the dilation and constriction of blood vessels in the head. Investigators now believe that migraine is caused by inherited abnormalities in genes that control the activities of certain cell populations in the brain. The International Headache Society (IHS, 1988) classifies migraine with aura (classical migraine) and migraine without aura (common migraine) as the major types of migraine.

Activity in any of the above-mentioned indications can of course be determined by carrying out suitable clinical trials in a manner known to a person skilled in the relevant art for the particular indication and/or in the design of clinical trials in general.

The compounds of formula I according to the invention may advantageously be used in conjunction with one or more other therapeutic agents. In particular the compounds according to the invention may be used in conjunction with one or more other therapeutic agents linked to the cholinergic transmission: e.g. agonists/antagonists to M1, M2, M3, M4, M5 receptors and to nicotinic receptors, and acetylcholinesterase modulators.

The compounds of formula I according to the invention may be used in conjunction with one or more other therapeutic agents linked to the adrenergic/noradrenergic transmission: e.g. agonists/antagonists to $\alpha 1, \alpha 2, \beta 1, \beta 2, \beta 3$ receptors, MAO (type A and B) and COMT modulators.

The compounds of formula I according to the invention may be used in conjunction with one or more other therapeutic agents linked to dopaminergic transmission: e.g. agonists/antagonists to dopamine D1, D2, D3, D4, and D5 receptors, tyrosine-hydroxylase and DOPA-decarboxylase modulators, and vesicle monoamines transporters modulators.

The compounds of formula I according to the invention may be used in conjunction with one or more other therapeutic agents linked to serotoninergic transmission: e.g. agonists/antagonists to $5-HT_1$, $5-HT_2$, $5-HT_3$, $5-HT_4$, $5-HT_5$, $5-HT_6$ and $5-HT_7$ receptors.

The compounds of formula I according to the invention may be used in conjunction with one or more other therapeutic agents linked to histaminergic transmission: e.g. agonists/antagonists to $H_1$, $H_2$, $H_3$ and $H_4$ receptors.

The compounds of formula I according to the invention may be used in conjunction with one or more other therapeutic agents linked to glutamatergic transmission: e.g. agonists/antagonists to AMPA receptors (GluR1, GluR2, GluR3, GluR4); kaïnate receptors (GluR5, GluR6, GluR7 and KA1, KA2); NMDA receptors (subunits NR1, NR2A, NR2B, NR2C, NR2D and NR3A).

The compounds of formula I according to the invention may be used in conjunction with one or more other therapeutic agents linked to gabaergic transmission: e.g. agonists/antagonists to $GABA_{A1}$ to $GABA_{A6}$, $GABA_{A0}$, $GABA_C$ and $GABA_B$, or agents enhancing the production or reducing the degradation or the re-uptake of GABA such as vaproate, vigabatrin or tiagabine.

The compounds of formula I according to the invention may be used in conjunction with one or more other therapeutic agents such as $CB_1$ agonists, VR1 agonists, SV2 ligands such as levetiracetam, (2S)-2-[(4R)-2-oxo-4-propylpyrrolidin-1-yl]butanamide or (2S)-2-[(4S)-4-(2,2-difluorovinyl)-2-oxopyrrolidin-1-yl]butanamide, amantadine, or NMDA/AMPA antagonists.

Activity in any of the above-mentioned indications can of course be determined by carrying out suitable clinical trials in a manner known to a person skilled in the relevant art for the particular indication and/or in the design of clinical trials in general.

For treating diseases, compounds of formula I or their pharmaceutically acceptable salts may be employed at an effective daily dosage and administered in the form of a pharmaceutical composition.

Therefore, another embodiment of the present invention concerns a pharmaceutical composition comprising an effective amount of a compound of formula I or pharmaceutically acceptable salts thereof in combination with a pharmaceutically acceptable diluent or carrier.

To prepare a pharmaceutical composition according to the invention, one or more of the compounds of formula I or a pharmaceutically acceptable salt thereof is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, parenteral or intranasal.

Pharmaceutical compositions comprising compounds according to the invention can, for example, be administered orally or parenterally, i.e., intravenously, intramuscularly or subcutaneously, intrathecally, by inhalation or intranasally.

Pharmaceutical compositions suitable for oral administration can be solids or liquids and can, for example, be in the form of tablets, pills, dragees, gelatin capsules, solutions, syrups, chewing-gums and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula I in compositions for oral administration is at least 0.5% by weight and can be up to 80% by weight with respect to the total weight of the composition.

For the preferred oral compositions, the daily dosage is in the range 5 to 5000 milligrams (mg) of compounds of formula I.

In compositions for parenteral administration, the quantity of compound of formula I present is at least 0.5% by weight and can be up to 33% by weight with respect to the total weight of the composition. For the preferred parenteral compositions, the dosage unit is in the range 5 mg to 500 mg of compounds of formula I.

The daily dose can fall within a wide range of dosage units of compound of formula I and is generally in the range 3 to 7000 mg, and preferably 5 to 500 mg. However, it should be understood that the specific doses can be adapted to particular cases depending on the individual requirements, at the physician's discretion.

The following examples are provided for illustrative purposes.

Unless specified otherwise in the examples, characterization of the compounds is performed according to the following methods:

NMR spectra are recorded on a BRUKER AC 250 Fourier Transform NMR Spectrometer fitted with an Aspect 3000 computer and a 5 mm $^1H/^{13}C$ dual probehead or BRUKER DRX 400 FT NMR fitted with a SG Indigo$^2$ computer and a 5 mm inverse geometry $^1H/^{13}C/^{15}N$ triple probehead. The compound is studied in DMSO-$d_6$ (or CDCl$_3$) solution at a probe temperature of 313 K or 300 K and at a concentration of 20 mg/ml. The instrument is locked on the deuterium signal of DMSO-$d_6$ (or CDCl$_3$). Chemical shifts are given in ppm downfield from TMS taken as internal standard.

HPLC analyses are performed using one of the following systems:

an Agilent 1100 series HPLC system mounted with an INERTSIL ODS 3 C18, DP 5 μm, 250×4.6 mm column. The gradient runs from 100% solvent A (acetonitrile, water, H$_3$PO$_4$ (5/95/0.001, v/v/v)) to 100% solvent B (acetonitrile, water, H$_3$PO$_4$ (95/5/0.001, v/v/v)) in 6 min with a hold at 100% B of 4 min. The flow rate is set at 2.5 ml/min. The chromatography is carried out at 35° C.

a HP 1090 series HPLC system mounted with a HPLC Waters Symmetry C18, 250×4.6 mm column. The gradient runs from 100% solvent A (MeOH, water, H$_3$PO$_4$ (15/85/0.001M, v/v/M)) to 100% solvent B (MeOH, water, H$_3$PO$_4$ (85/15/0.001 M, v/v/M)) in 10 min with a hold at 100% B of 10 min. The flow rate is set at 1 ml/min. The chromatography is carried out at 40° C.

Mass spectrometric measurements in LC/MS mode are performed as follows:

HPLC Conditions

Analyses are performed using a WATERS Alliance HPLC system mounted with an INERTSIL ODS 3, DP 5 μm, 250× 4.6 mm column.

The gradient runs from 100% solvent A (acetonitrile, water, TFA (10/90/0.1, v/v/v)) to 100% solvent B (acetonitrile, water, TFA (90/10/0.1, v/v/v)) in 7 min with a hold at 100% B of 4 min. The flow rate is set at 2.5 ml/min and a split of 1/25 is used just before API source.

MS Conditions

Samples are dissolved in acetonitrile/water, 70/30, v/v at the concentration of about 250 μgr/ml. API spectra (+ or −) are performed using a FINNIGAN (San Jose, Calif., USA) LCQ ion trap mass spectrometer. APCI source operates at 450° C. and the capillary heater at 160° C. ESI source operates at 3.5 kV and the capillary heater at 210° C.

Mass spectrometric measurements in DIP/EI mode are performed as follows: samples are vaporized by heating the probe from 50° C. to 250° C. in 5 min. EI (Electron Impact) spectra are recorded using a FINNIGAN (San Jose, Calif., USA) TSQ 700 tandem quadrupole mass spectrometer. The source temperature is set at 150° C.

Mass spectrometric measurements on a TSQ 700 tandem quadrupole mass spectrometer (Finnigan MAT, San Jose, Calif., USA) in GC/MS mode are performed with a gas chromatograph model 3400 (Varian, Walnut Creek, Calif., USA) fitted with a split/splitless injector and a DB-5MS fused-silica column (15 m×0.25 mm I.D., 1 μm) from J&W Scientific (Folsom, Calif., USA). Helium (purity 99.999%) is used as carrier gas. The injector (CTC A200S autosampler) and the transfer line operate at 290 and 250° C., respectively. Sample (1 μl) is injected in splitless mode and the oven temperature is programmed as follows: 50° C. for 5 min., increasing to 280° C. (23° C./min) and holding for 10 min. The TSQ 700 spectrometer operates in electron impact (EI) or chemical ionization (CI/CH$_4$) mode (mass range 33-800, scan time 1.00 sec). The source temperature is set at 150° C.

Preparative chromatographic separations are performed on silicagel 60 Merck, particle size 15-40 μm, reference 1.15111.9025, using Novasep axial compression columns (80 mm i.d.), flow rates between 70 and 150 ml/min. Amount of silicagel and solvent mixtures as described in individual procedures.

The following abbreviations are used in the examples:

| | |
|---|---|
| AcOEt | Ethyl acetate |
| AcOH | Acetic acid |
| DMF | N,N-Dimethylformamide |
| DMSO | Dimethyl sulfoxide |
| NCS | N-chlorosuccinimide |

EXAMPLE 1

Synthesis of 2-(4-fluoro-2-oxo-2,3-dihydro-1H-indol-1-yl)acetamide 9

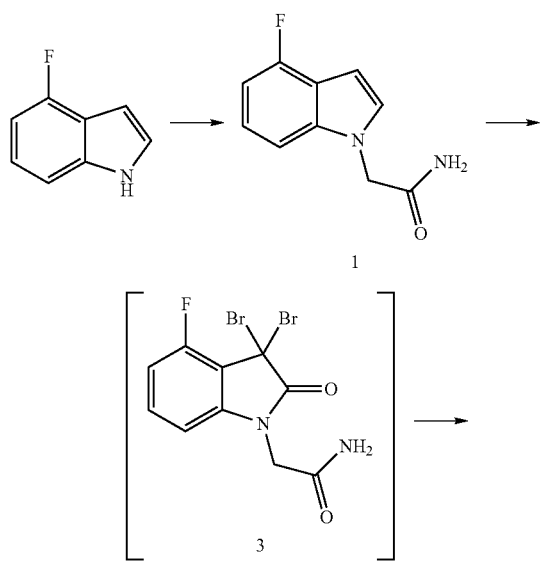

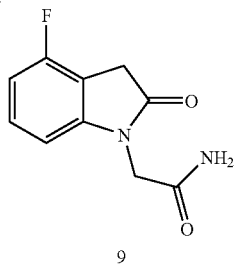

1.1 Synthesis of 2-(4-fluoro-1H-indol-1-yl)acetamide 1

A dispersion of 60% NaH in oil (0.387, 9.7 mmol) is added to an ice-cooled solution of 4-fluoroindole (1.007 g, 7.5 mmol) in dry DMF (10 ml). The stirring is continued for 20 minutes at room temperature, and the mixture is cooled again with an ice bath. After portionwise addition of solid 2-bromoacetamide (1.22 g, 9 mmol), the reaction mixture is stirred for 1.5 h at room temperature, then poured into cold water and extracted 3 times with AcOEt. The combined organic phases are dried over Na$_2$SO$_4$, filtered and concentrated in vacuo. The 2-(4-fluoro-1H-indol-1-yl)acetamide 1 is used as such in the next step.

MS (LC-MS, MH$^+$): 193.

2-(4-chloro-1H-indol-1-yl)acetamide 2 (MS (LC-MS, MH$^+$): 209/211)) and 2-[4-(trifluoromethyl)-1H-indol-1-yl]acetamide 2a can be synthesized according to the same method.

1.2 Synthesis of 2-(4-fluoro-2-oxo-2,3-dihydro-1H-indol-1-yl)acetamide 9

Pyridinium bromide perbromide (4.36 g, 13.74 mmol) is added in portions over a period of 0.5 h to a stirred solution of 2-(5-fluoro-1H-indol-1-yl)acetamide 1 (1.32 g, 6.87 mmol) in tert-butanol/H$_2$O (14 ml/1 ml) at room temperature. The reaction mixture is stirred for 0.5 h, then poured into water and diluted with AcOEt. After removal of the organic layer, the aqueous phase is extracted twice with AcOEt. Combined organic phases are dried over Na$_2$SO$_4$ and concentrated. 2-(3,3-dibromo-4-fluoro-2-oxo-2,3-dihydro-1H-indol-1-yl)acetamide 3 is obtained as a yellow solid and is directly used in the next step.

Zinc dust (4.46 g, 0.068 mol) is added to a stirred solution of the crude 2-(3,3-dibromo-4-fluoro-2-oxo-2,3-dihydro-1H-indol-1-yl)acetamide 3 (theorical: 6.32 mmol) in AcOH (20 ml) at 0° C. After 1 hour, the reaction mixture is filtered through a Celite pad. The filtrate is diluted with AcOEt and cold water. The pH is adjusted to 7 and the layers are separated. The aqueous phase is extracted again with AcOEt. Organic layers are dried over Na$_2$SO$_4$ and concentrated. Several attempts to cristallize in AcOEt failed. The crude reaction mixture is purified by reverse phase HPLC (LC-MS, acetonitrile/H$_2$O). 2-(4-fluoro-2-oxo-2,3-dihydro-1H-indol-1-yl)acetamide 9 is obtained as a white solid.

Yield: 0.072 g (5.3%).

MS (LC-MS, MH$^+$): 209.

The same experimental procedure is used for the synthesis of 2-(4-chloro-2-oxo-2,3-dihydro-1H-indol-1-yl)acetamide 7 (Yield: 21%; MS (LC-MS, MH$^+$): 223/225) from 2-(4-chloro-1H-indol-1-yl)acetamide 2 (3.27 g; 15.67 mmol); in that reaction, 2-(5-bromo-4-chloro-2-oxo-2,3-dihydro-1H-indol-1-yl)acetamide 8 is isolated as a side product (Yield: 15%; MS (LC-MS, MH+): 303/305).

EXAMPLE 2

Synthesis of 2-(4,5-dichloro-2-oxo-2,3-dihydro-1H-indol-1-yl)acetamide 10

2-(4-chloro-2-oxo-2,3-dihydro-1H-indol-1-yl)acetamide 7 (0.205 g, 0.9 mmol) is dissolved in 90% $H_2SO_4$ (1 ml) at room temperature, and NCS (0.12 g, 0.9 mmol) is slowly added with stirring. After 2 hours, the mixture is poured into cold water. The precipitate is collected, washed several times with water and then with $Et_2O$. The crude reaction mixture is purified by column chromatography on silicagel ($CH_2Cl_2$/EtOH/$NH_4OH$: 94.5/5/0.5 (v/v)) to afford the 2-(4,5-dichloro-2-oxo-2,3-dihydro-1H-indol-1-yl)acetamide 10 as a white solid.

Yield: 27 mg (11%).
MS (LC-MS, MH+): 259/261.

EXAMPLE 3

Synthesis of 2-(5-chloro-3,3-difluoro-2-oxo-2,3-dihydro-1H-indol-1-yl)acetamide 12

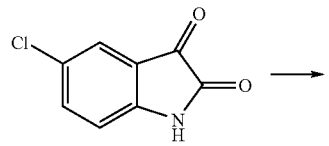

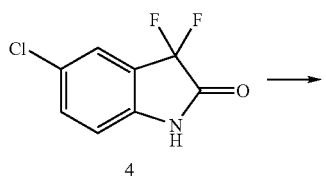

4

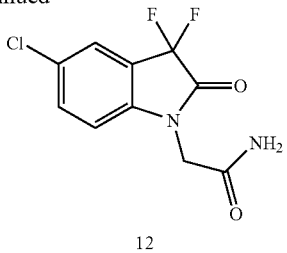

12

3.1 Synthesis of 5-chloro-3,3-difluoro-1,3-dihydro-2H-indol-2-one 4

5-chloro-1H-indole-2,3-dione (3.69 g, 0.020 mol) is dissolved in $CH_2Cl_2$ (200 ml) under inert atmosphere. (Diethylamino)sulfur trifluoride (8.3 ml, 0.063 mol) is rapidly added. The reaction is stirred at room temperature for 2 h. MeOH (80 ml) is added at 0° C. and stirring is continued for 0.25 h. Then water is added and the mixture is extracted with $CH_2Cl_2$. The combined organic phases are dried over $Na_2SO_4$ and concentrated in vacuo. The obtained orange solid is purified by flash chromatography on silica gel (Hexane/EtOAc 75/25) to give 5-chloro-3,3-difluoro-1,3-dihydro-2H-indol-2-one 4 as a yellow solid.

Yield: 2.56 g (62%).
$^1$H NMR ($\delta$ (400 MHz), DMSO-$d_6$): 3.29 (s, 1H); 6.97 (ddd, 1H) 7.535 (m, 1H); 7.79 (dd, 1H).

3,3,5-trifluoro-1,3-dihydro-2H-indol-2-one 6 can be synthesized according to the same method ($^1$H NMR ($\delta$ (400 MHz), DMSO-$d_6$): 7.04 (m, 1H); 7.39 (m, 1H); 7.66 (m, 1H)).

3.2 Synthesis of 2-(5-chloro-3,3-difluoro-2-oxo-2,3-dihydro-1H-indol-1-yl)acetamide 12

5-chloro-3,3-difluoro-1,3-dihydro-2H-indol-2-one 4 (2.55 g, 12.5 mmol) is dissolved in dry DMF (20 ml) under a nitrogen atmosphere. The solution is cooled at 0° C. and NaH (0.547 g, 13.8 mmol, 60% dispersion) is carefully added portionwise. When the nitrogen evolution ceases, bromoacetamide (2.05 g, 15.0 mmol) is added. After 30 minutes, the mixture is poured into cold water and the solid is filtered off and washed with water. The crude material is directly recrystallized in acetone/water affording of 2-(5-chloro-3,3-difluoro-2-oxo-2,3-dihydro-1H-indol-1-yl)acetamide 12 as a pink solid.

Yield: 0.69 g (21%).
MS (GC-MS, M+): 260/262.

Compounds described in table 1 may be prepared according to one of the previous methods.

TABLE 1

| n° | Configuration | IUPAC Name | MH+ |
|---|---|---|---|
| 7 | achiral | 2-(4-chloro-2-oxo-2,3-dihydro-1H-indol-1-yl)acetamide | 223/225 |
| 8 | achiral | 2-(5-bromo-4-chloro-2-oxo-2,3-dihydro-1H-indol-1-yl)acetamide | 303/305 |
| 9 | achiral | 2-(4-fluoro-2-oxo-2,3-dihydro-1H-indol-1-yl)acetamide | 209 |
| 10 | achiral | 2-(4,5-dichloro-2-oxo-2,3-dihydro-1H-indol-1-yl)acetamide | 259/261 |
| 11 | achiral | 2-(3,3-difluoro-2-oxo-2,3-dihydro-1H-indol-1-yl)acetamide | 226 (GC-MS, M+·) |

TABLE 1-continued

| n° | Configuration | IUPAC Name | MH+ |
|---|---|---|---|
| 12 | achiral | 2-(5-chloro-3,3-difluoro-2-oxo-2,3-dihydro-1H-indol-1-yl)acetamide | 260/262 (GC-MS, M+·) |
| 13 | achiral | 2-(5-bromo-3,3-difluoro-2-oxo-2,3-dihydro-1H-indol-1-yl)acetamide | 304/306 (GC-MS, M+·) |
| 14 | achiral | 2-(3,3-difluoro-5-methyl-2-oxo-2,3-dihydro-1H-indol-1-yl)acetamide | 241 |
| 15 | achiral | 2-(3,3,5-trifluoro-2-oxo-2,3-dihydro-1H-indol-1-yl)acetamide | 244 (GC-MS, M+·) |
| 16 | achiral | 2-[2-oxo-4-(trifluoromethyl)-2,3-dihydro-1H-indol-1-yl]acetamide | 259 |

EXAMPLE 4

Pharmacological Testing—Hemi-Parkinsonian Rat Model

The invention is based upon our studies relating the use of active compounds to prolong L-DOPA activity when its action is diminishing in a rat model of Parkinson's disease.

This study is designed to investigate whether the compounds of the invention prolong L-DOPA activity using the hemi-parkinsonian rat model.

Using stereotaxic surgery in the rats, 6-hydroxydopamine (6-OHDA), a specific toxin to dopamine nerve cells, is delivered directly along the nigrostriatal pathway (medial forebrain bundle). Uptake of 6-OHDA leads to the death of dopamine nerve cells resulting in damage similar to that in PD (the abbreviation "PD" means Parkinson's disease). In the rat, destruction of the nerve cells on one side of the brain creates an imbalance in the basal ganglia that causes the rat to spontaneously turn in a circular fashion towards the destroyed side (ipsilateral rotations). Drugs that stimulate receptor sites normally targeted by dopamine (e.g. dopamine agonist or L-DOPA) cause the rat to turn in a direction opposite to the destroyed side (contralateral rotations). The contralateral rotation response provides a behavioural index of dopamine denervation receptor supersensitivity.

The study is performed on 16 male Sprague-Dawley rats. The animals have an average weight of 270 g at surgery and 350 g during the behavioural experiments. To lesion the ascending dopaminergic nigro-stiratal pathway, rats are anaesthetized with ketamine (75 mg/kg, ip) and xylazine (10 mg/kg, ip) and placed in a stereotaxic frame. 6-OHDA (10 μg/rat) is injected unilaterally into the right medial forebrain bundle.

To protect noradrenergic neurons, rats are pre-treated with imipramine (15 mg/kg, ip). Two weeks after surgery, rats are challenged with 100 mg/kg i.p. L-DOPA using eight identical automated rotometers in order to select them for the test. Only rats showing at least 150 contralateral rotations within 60 min are accepted for the test. The test starts one week after the selection.

The testing day, all lesioned animals are put in the testing room 15 minutes for acclimation. Eight rats are injected either with vehicle (DMSO, i.p.) or with a compound of the invention (test compound: 100 mmol/kg, i.p.) 15 minutes before the L-DOPA injection and are replaced in their home cage. After the L-DOPA injection (50 mg/kg, i.p.) they are put directly into the rotometers. Contralateral rotations start to be recorded after a 10-min acclimation period in the arenas.

Analyses are conducted on the data recorded for 120 min. Data are analyzed with a mixed-model analysis of variance (ANOVA) incorporating the treatment as between-group factor (treatment: 2 levels: vehicle and test compound) and the successive twelve measurements of contralateral rotations as within-subjects factor (time, 12 levels). The reliabilities of the between-mean differences within a time-sample were assessed with planned contrasts using a F statistic.

The major benefit of compounds of the invention is a prolongation of L-DOPA-induced contralateral rotation during the second hour post-drug administration without rise of the side-effect (abnormal involuntary movements were not increased).

Thus the clinical benefit for compounds of the invention is as an adjunctive therapy to reduce motor fluctuation (i.e. "end-of-dose wearing-off") and thus to increase "on-time" in parkinsonian patients exposed to dopamine-replacement therapy. Additionally, the extension of 'on-time' and the potential for L-DOPA sparing represents a useful de novo therapy to delay the onset of dyskinesia.

The invention claimed is:

1. A method of treating, ameliorating, or inhibiting the effects of movement disorders and/or motor fluctuations in a subject suffering from Parkinson's disease, the method comprising administering to the subject an effective amount of a compound of formula I,

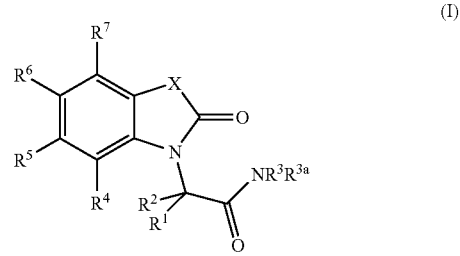

(I)

wherein

X is $CH_2$ or $CF_2$;

$R^1$ is selected from hydrogen or $C_{1-4}$ alkyl optionally substituted by at least one hydroxy;

$R^2$ is selected from hydrogen or $C_{1-4}$ alkyl optionally substituted by at least one hydroxy;

$R^3$ is selected from hydrogen or unsubstituted $C_{1-4}$ alkyl;

$R^{3a}$ is selected from hydrogen or unsubstituted $C_{1-4}$ alkyl;

$R^4$ is selected from hydrogen; halogen; $C_{1-4}$ alkyl optionally substituted by at least a group selected independently from halogen and a phenyl group; or $C_{1-4}$ alkoxy optionally substituted by at least a group selected independently from halogen, $C_{1-4}$ alkoxy and a phenyl group;

$R^5$ is selected from hydrogen; halogen; $C_{1-4}$ alkyl optionally substituted by at least a group selected independently from halogen and a phenyl group; or $C_{1-4}$ alkoxy optionally substituted by at least a group selected independently from halogen, $C_{1-4}$ alkoxy and a phenyl group;

$R^6$ is selected from hydrogen; halogen; $C_{1-4}$ alkyl optionally substituted by at least a group selected independently from halogen and a phenyl group; or $C_{1-4}$ alkoxy optionally substituted by at least a group selected independently from halogen, $C_{1-4}$ alkoxy and a phenyl group;

$R^7$ is selected from hydrogen; halogen; $C_{1-4}$ alkyl optionally substituted by at least a group selected independently from halogen and a phenyl group; or $C_{1-4}$ alkoxy optionally substituted by at least a group selected independently from halogen, $C_{1-4}$ alkoxy and a phenyl group;

with the proviso that if X is $CH_2$, then $R^7$ is different from hydrogen;

or a pharmaceutically acceptable salt thereof or a stereoisomeric forms thereof.

2. The method according to claim 1, wherein X is $CH_2$ and $R^7$ is halogen; $C_{1-4}$ alkyl optionally substituted by at least a group selected independently from halogen and a phenyl group; or $C_{1-4}$ alkoxy optionally substituted by at least a group selected independently from halogen, $C_{1-4}$ alkoxy and a phenyl group.

3. The method according to claim 1, wherein X is $CF_2$.

4. The method according to claim 1, wherein
X is $CH_2$ or $CF_2$;
$R^1$ is selected from hydrogen or unsubstituted $C_{1-4}$ alkyl;
$R^2$ is selected from hydrogen or unsubstituted $C_{1-4}$ alkyl;
$R^1$ is selected from hydrogen or unsubstituted $C_{1-4}$ alkyl;
$R^{3a}$ is selected from hydrogen or unsubstituted $C_{1-4}$ alkyl;
$R^4$ is selected from hydrogen; halogen; unsubstituted $C_{1-4}$ alkyl; or unsubstituted $C_{1-4}$ alkoxy;
$R^5$ is selected from hydrogen; halogen; unsubstituted $C_{1-4}$ alkyl; or unsubstituted $C_{1-4}$ alkoxy;
$R^6$ is selected from hydrogen; halogen; unsubstituted $C_{1-4}$ alkyl; or unsubstituted $C_{1-4}$ alkoxy;
$R^7$ is selected from hydrogen; halogen; unsubstituted $C_{1-4}$ alkyl; trifluoromethyl; or unsubstituted $C_{1-4}$ alkoxy.

5. The method according to claim 1, wherein X is $CH_2$ or $CF_2$; $R^1$, $R^2$, $R^3$, $R^{3a}$, $R^4$ and $R^5$ are hydrogen; and $R^6$ is hydrogen, methyl, bromine, chlorine or fluorine; and $R^7$ is hydrogen, chlorine, fluorine or trifluoromethyl.

6. The method according to claim 1, wherein X is $CH_2$; $R^1$, $R^2$, $R^3$, $R^{3a}$, $R^4$ and $R^5$ are hydrogen; $R^6$ is hydrogen, chlorine or bromine; and $R^7$ is chlorine or fluorine.

7. The method according to claim 1, wherein X is $CH_2$; $R^1$, $R^2$, $R^3$, $R^{3a}$, $R^4$ and $R^5$ are hydrogen; $R^6$ is hydrogen; and $R^7$ is fluorine.

8. The method according to claim 1, wherein X is $CF_2$; $R^1$, $R^2$, $R^3$, $R^{3a}$, $R^4$ and $R^5$ are hydrogen; $R^6$ is chlorine or fluorine; and $R^7$ is hydrogen.

9. A method of treating, ameliorating, or inhibiting the effects of movement disorders and/or motor fluctuations in a subject suffering from Parkinson's disease, the method comprising administering to the subject an effective amount of a compound selected from 2-(4-chloro-2-oxo-2,3-dihydro-1H-indol-1-yl)acetamide;
2-(5-bromo-4-chloro-2-oxo-2,3-dihydro-1H-indol-1-yl)acetamide;
2-(4-fluoro-2-oxo-2,3-dihydro-1H-indol-1-yl)acetamide;
2-(4,5-dichloro-2-oxo-2,3-dihydro-1H-indol-1-yl)acetamide;
2-(3,3-difluoro-2-oxo-2,3-dihydro-1H-indol-1-yl)acetamide;
2-(5-chloro-3,3-difluoro-2-oxo-2,3-dihydro-1H-indol-1-yl)acetamide;
2-(5-bromo-3,3-difluoro-2-oxo-2,3-dihydro-1H-indol-1-yl)acetamide;
2-(3,3-difluoro-5-methyl-2-oxo-2,3-dihydro-1H-indol-1-yl)acetamide;
2-(3,3,5-trifluoro-2-oxo-2,3-dihydro-1H-indol-1-yl)acetamide; and
2-[2-oxo-4-(trifluoromethyl)-2,3-dihydro-1H-indol-1-yl]acetamide;

or a pharmaceutically acceptable salt thereof or a stereoisomeric form thereof.

10. A method of treating, ameliorating, or inhibiting the effects of movement disorders and/or motor fluctuations in a subject suffering from Parkinson's disease, the method comprising administering to the subject an effective amount of a compound selected from 2-(4-chloro-2-oxo-2,3-dihydro-1H-indol-1-yl)acetamide;
2-(4-fluoro-2-oxo-2,3-dihydro-1H-indol-1-yl)acetamide;
2-(5-chloro-3,3-difluoro-2-oxo-2,3-dihydro-1H-indol-1-yl)acetamide; and
2-(5-bromo-3,3-difluoro-2-oxo-2,3-dihydro-1H-indol-1-yl)acetamide;

or a pharmaceutically acceptable salt thereof or a stereoisomeric form thereof.

11. A method of treating, ameliorating, or inhibiting the effects of movement disorders and/or motor fluctuations in a subject suffering from Parkinson's disease, the method comprising administering to the subject an effective amount of 2-(4-fluoro-2-oxo-2,3-dihydro-1H-indol-1-yl)acetamide or a pharmaceutically acceptable salt thereof or a stereoisomeric form thereof.

* * * * *